United States Patent
Li et al.

(10) Patent No.: US 9,808,610 B2
(45) Date of Patent: *Nov. 7, 2017

(54) METHOD AND DEVICE FOR TISSUE REMOVAL AND FOR DELIVERY OF A THERAPEUTIC AGENT OR BULKING AGENT

(71) Applicant: Boston Scientific Scimed Inc., Maple Grove, MN (US)

(72) Inventors: Jianmin Li, Lexington, MA (US); Weenna Bucay-Couto, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 999 days.

This patent is subject to a terminal disclaimer.

(21) Appl. No.: 13/970,675

(22) Filed: Aug. 20, 2013

(65) Prior Publication Data

US 2013/0338570 A1     Dec. 19, 2013

Related U.S. Application Data

(63) Continuation of application No. 12/893,168, filed on Sep. 29, 2010, now Pat. No. 8,517,994, which is a
(Continued)

(51) Int. Cl.
*A61M 37/00*     (2006.01)
*A61B 17/22*     (2006.01)
(Continued)

(52) U.S. Cl.
CPC ............. *A61M 37/00* (2013.01); *A61B 17/22* (2013.01); *A61B 17/32002* (2013.01);
(Continued)

(58) Field of Classification Search
CPC .... A61M 37/00; A61B 10/0241; A61B 17/22; A61B 17/32002; A61B 2017/00274;
(Continued)

(56) References Cited

U.S. PATENT DOCUMENTS 2,850,007 A * 9/1958 Lingley .............. A61B 10/0266
                                                    600/567
3,732,858 A * 5/1973 Banko ................ A61B 10/0266
                                                    600/566
(Continued)

FOREIGN PATENT DOCUMENTS

WO        9424941 A1    11/1994

OTHER PUBLICATIONS

C. Lowell Parsons, "Evidence-based strategies for recognizing and managing IC", Contemporary Urology, vol. 15, No. 2, Feb. 2003, pp. 22-35.
(Continued)

*Primary Examiner* — Quynh-Nhu H Vu
(74) *Attorney, Agent, or Firm* — Bookoff McAndrews, PLLC

(57) ABSTRACT

According to an aspect of the present invention, a medical device is provided, which comprises the following: (a) a hollow elongate body (e.g., a elongate cylinder, such as a needle) having distal and proximal ends; and (b) a rotatable member comprising a tissue morselizer and an elongate shaft (e.g., an auger-like tissue-drilling bit). In the devices of the present invention, the elongate shaft is disposed within the hollow elongate body and cooperates with the hollow elongate body to (i) advance material (e.g., morselated tissue) toward the proximal end of the hollow elongate body when the shaft is rotated in a first direction, and (ii) advance material (e.g., a therapeutic agent and/or a bulking agent) toward the distal end of the hollow elongate body when the
(Continued)

shaft is rotated in a second direction that is opposite the first direction. According to another aspect of the invention a method of treatment is provided that comprises: (a) inserting the a medical device like that above into the tissue of a patient; (b) morselizing and removing tissue from within the patient while rotating the shaft in a first direction, thereby creating a void within the patient; and (c) introducing a therapeutic agent and/or a bulking agent into the void.

18 Claims, 2 Drawing Sheets

Related U.S. Application Data continuation of application No. 11/124,827, filed on May 9, 2005, now Pat. No. 7,806,871.

(51) Int. Cl.
  *A61B 17/32* (2006.01)
  *A61B 10/02* (2006.01)
  *A61B 17/00* (2006.01)
  *A61B 17/3207* (2006.01)
  *A61B 18/00* (2006.01)

(52) U.S. Cl.
  CPC . *A61B 10/0241* (2013.01); *A61B 2017/00274* (2013.01); *A61B 2017/00685* (2013.01); *A61B 2017/320775* (2013.01); *A61B 2018/00547* (2013.01)

(58) Field of Classification Search
  CPC .. A61B 17/00685; A61B 2017/320775; A61B 2018/00547
  See application file for complete search history.

(56) References Cited

U.S. PATENT DOCUMENTS

| | | | |
|---|---|---|---|
| 3,976,077 A | | 8/1976 | Kerfoot, Jr. |
| 4,436,091 A | | 3/1984 | Banko |
| 5,234,426 A | | 8/1993 | Rank et al. |
| 5,569,178 A | * | 10/1996 | Henley ............ A61B 17/32002 604/22 |
| 5,591,187 A | | 1/1997 | Dekel |
| 6,156,049 A | * | 12/2000 | Lovato ................ A61B 1/015 604/22 |
| 6,443,966 B1 | * | 9/2002 | Shiu ............... A61B 17/320758 606/159 |
| 6,491,672 B2 | | 12/2002 | Slepian et al. |
| 6,503,353 B1 | | 1/2003 | Peterson et al. |
| 6,517,519 B1 | | 2/2003 | Rosen et al. |
| 6,642,274 B1 | | 11/2003 | Neal |
| 6,749,617 B1 | * | 6/2004 | Palasis ............... A61B 17/3468 606/167 |
| 6,846,314 B2 | * | 1/2005 | Shapira ............... A61B 10/025 604/35 |
| 7,806,871 B2 | * | 10/2010 | Li ..................... A61B 17/32002 604/164.06 |
| 7,905,896 B2 | * | 3/2011 | Straub ............ A61B 17/320783 606/159 |
| 8,114,106 B2 | | 2/2012 | Straub |
| 8,517,994 B2 | * | 8/2013 | Li ..................... A61B 17/32002 604/164.06 |
| 2001/0047147 A1 | | 11/2001 | Slepian et al. |
| 2002/0138021 A1 | * | 9/2002 | Pflueger ............ A61B 10/0266 600/565 |
| 2003/0050638 A1 | | 3/2003 | Yachia et al. |
| 2003/0100830 A1 | | 5/2003 | Zhong et al. |
| 2003/0114875 A1 | * | 6/2003 | Sjostrom .......... A61B 17/32002 606/170 |
| 2003/0171678 A1 | | 9/2003 | Batten et al. |
| 2004/0219028 A1 | * | 11/2004 | Demarais ....... A61B 17/320725 417/53 |
| 2005/0027265 A1 | * | 2/2005 | Maki ................ A61B 17/32037 604/267 |
| 2005/0064008 A1 | | 3/2005 | Bucay-Couto et al. |
| 2005/0064045 A1 | | 3/2005 | Zhong et al. |
| 2005/0165329 A1 | | 7/2005 | Taylor et al. |
| 2011/0125088 A1 | * | 5/2011 | Dixon ................ A61B 17/8822 604/82 |

OTHER PUBLICATIONS

C. Lowell Parsons et al., "Gynecologic Presentation of Interstitial Cystitis as Detected by Intravesical Potassium Sensitivity", Obstetrics & Gynocology, vol. 98, No. 1, Jul. 2001, pp. 127-132.

C. Lowell Parsons et al., "The prevalence of interstitial cystitis in gynecologic patients with pelvic pain, as detected by intravesical potassium sensitivity", American Journal of Obstetrics and Gynecology, vol. 187, No. 5, Nov. 2002, pp. 1395-1400.

* cited by examiner

METHOD AND DEVICE FOR TISSUE REMOVAL AND FOR DELIVERY OF A THERAPEUTIC AGENT OR BULKING AGENT

RELATED APPLICATIONS

The present application is a continuation of co-pending U.S. patent application Ser. No. 12/893,168, filed Sep. 29, 2010, the disclosure of which is hereby incorporated by reference in its entirety, and which claims the benefit of continuation U.S. patent application Ser. No. 11/124,827, filed May 9, 2005, now U.S. Pat. No. 7,806,871 which is incorporated by reference in its entirety herein.

FIELD OF THE INVENTION

The present invention relates to devices and methods for removal of tissue from a patient, and for delivery of a therapeutic agent or bulking agent to the patient.

BACKGROUND OF THE INVENTION

Various diseases and conditions are known which are treated by the removal of tissue. Some specific examples include prostate diseases such as prostatitis, benign prostatic hypertrophy (BPH), prostatodynia, and prostate carcinoma, which afflict many adult males. The largest population of men stricken with prostate problems is men over age fifty, although inherited prostate problems can appear in much younger men.

Unfortunately, therapeutic options for the above and many other diseases are limited, and many surgical options are invasive to neighboring tissue. For example, according to U.S. Pat. No. 6,642,274, surgical treatment of BPH is the most common surgery of men in the developed countries of the world, and the most common prostate surgery involves trans-urethral resection of the prostate (TURP), which is accomplished by resecting the prostatic tissues surrounding the urethra that cause obstruction. Unfortunately, although highly effective in reducing obstructions, the dominant mechanism behind TURP is the progressive coring-out of the prostate, beginning at the level of the urethra and progressing outward into the prostatic capsule. Hence, this surgical procedure is destructive to the urethra and carries various complications including urinary incontinence, retrograde ejaculation, and impotence.

SUMMARY OF THE INVENTION

According to an aspect of the present invention, medical devices are provided, which comprise the following: (a) a hollow elongate body having distal and proximal ends (e.g., an elongate cylinder, such as a needle, in accordance with certain embodiments of the invention); and (b) a rotatable member comprising a tissue morselizer and an elongate shaft (e.g., an auger-like tissue-drilling bit, in accordance with certain embodiments of the invention).

In the devices of the present invention, the elongate shaft is disposed within the hollow elongate body and cooperates with the hollow elongate body to (i) advance material (e.g., morselated tissue) toward the proximal end of the hollow elongate body when the shaft is rotated in a first direction, as well as to (ii) advance material (e.g., a therapeutic agent and/or a bulking agent) toward the distal end of the hollow elongate body when the shaft is rotated in a second direction that is opposite the first direction.

According to another aspect of the invention a method of treatment is provided that comprises: (a) inserting a medical device like that above into the tissue of a patient; (b) morselizing and removing tissue from within the patient while rotating the shaft in a first direction, thereby creating a void within the patient; and (c) introducing a therapeutic agent and/or bulking agent into the void, for example, while rotating the shaft in a second direction opposite the first direction.

Tissue that can be removed using the devices and methods of the present invention include, for example, prostate, brain, kidney, liver, bladder, damaged tissues, and other soft tissues such as tissues with cancers, among many others.

Therapeutic agents that can be introduced using the devices and methods of the present invention include, for example, necrosis agents (also referred to herein as ablation agents), hemostatic agents, anticoagulants, analgesics, antispasmodic agents, and antineoplastic agents, among many others. Dosage forms which can be delivered include liquid and semi-liquid dosage forms (e.g., solutions, emulsions, dispersions or gels) as well as semi-solid and solid dosage forms (e.g., particles, granules or pellets of material which may be rigid or deformable).

An advantage of the present invention is that novel devices and procedures are provided, which allow for the efficient removal of targeted tissue and efficient introduction of therapeutic and/or bulking agents, while minimizing collateral damage to neighboring tissue.

These and other aspects, embodiments and advantages of the present invention will become immediately apparent to those of ordinary skill in the art upon review of the Detailed Description and Claims to follow.

DETAILED DESCRIPTION OF THE INVENTION

According to an aspect of the present invention, novel medical devices are provided, which comprise: (a) a hollow elongate body and (b) a rotatable member comprising a tissue morselizer and an elongate shaft. The elongate shaft of the rotatable member and the hollow body cooperate with one another to advance material that is present within the hollow body (i) toward the proximal end of the hollow body when the shaft is rotated in a first direction, and (ii) toward the distal end of the hollow elongate body when the shaft is rotated in a second direction that is opposite the first direction.

In various embodiments, the hollow elongate body includes a hollow cylindrical portion, which is typically adapted for penetration of tissue. For example, the hollow elongate body can comprise a hollow needle having a beveled distal end. The hollow elongate body can be stiff or flexible, as desired. The length of the hollow body will vary widely and will depend, for example, upon the distance to the tissue of interest from the point of insertion of the needle. Where the hollow elongate body comprises a hollow needle, the needle size typically ranges from 10 to 22 gauge, more typically 12 to 18 gauge.

In some embodiments, the hollow body is provided with a side port that is adapted to receive and sever tissue. Side ports are well known in the biopsy needle art.

As noted above, the devices of the present invention include a rotatable member that comprises a tissue morselizer and an elongate shaft. As used herein, a "tissue morselizer" is a device which can cut, slice, chop, chip, grind, or otherwise break down tissue. For example, in some embodiments the tissue morselizer is adapted to grind tissue, in some embodiments, the tissue morselizer is adapted to slice tissue, and so forth.

The elongate shaft of the rotatable member cooperates with the hollow body to advance material that is present within the hollow body in a direction that is dependent upon the rotational direction of the shaft. For instance, when the shaft is rotated in a first direction (e.g., clockwise), material (e.g., morselized tissue) is transported from the distal end of the hollow body, which is inserted into the tissue, toward the proximal end of the same. Conversely, when the shaft is rotated in the opposite direction (e.g., counterclockwise), material (e.g., therapeutic agent and/or bulking agent) is transported from the proximal end of the hollow body toward the distal end of the same, or toward the void created.

Figure 1:
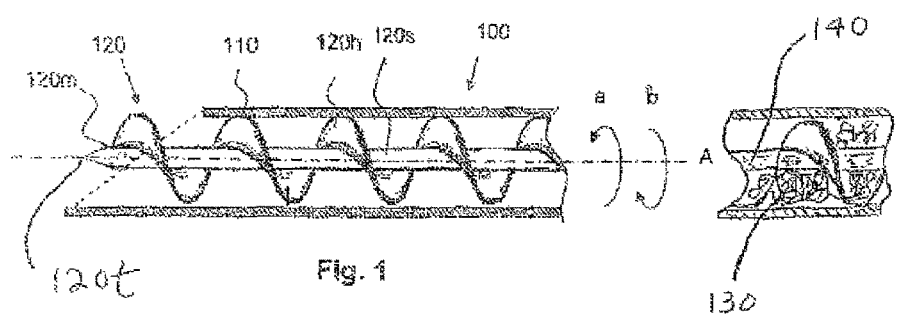
FIG. 1 is a schematic, partial cross-sectional illustration of the distal portion of a medical device, in accordance with an embodiment of the present invention.

In this regard, and in accordance with certain beneficial embodiments of the invention, the elongate shaft is provided with one or more raised helices, such as those that are found in augers (or screws). For example, FIG. 1 illustrates the distal end of a medical device 100 in accordance with a specific embodiment of the present invention. The medical device 100 includes a hollow elongate body 110 (e.g., a needle), which is provided with a beveled end to assist with tissue penetration. Disposed within the hollow elongate body 110 is a rotatable member 120 comprising a morselizer 120m having a pointed morselizing tip 120t (e.g., the cutting tip of an auger-type drilling bit), a central shaft 120s, and a raised helix 120h. (Note that the hollow elongate body 110 is shown in cross section, while the rotatable member 120 is not.) The rotatable member 120 in this embodiment is axially movable with respect to the hollow elongate body 110.

When the central shaft 120s is rotated in a first direction "a" around axis "A", the morselizer 120m engages and morselizes tissue that it contacts at its tip 120t. To enhance the morselizing action of the device, the blade that forms the raised helix 120h is provided with a sharp cutting edge, at least at the distal end of the device where tissue is engaged by the helix (i.e., on the left). Once morselized, tissue occupying the voids between the raised helix 120h is advanced from the distal end of the device 100 toward the proximal end of the device (i.e., toward the right). Conversely, when the central shaft 120s is rotated in direction "b," material 130 occupying within the voids between the raised helix 120h of the rotatable member 120 (e.g., therapeutic agent and/or bulking agent) is advanced from right to left through the cylinder of the hollow elongate body 110.

In some embodiments of the invention, the pitch of the helical blades at the end of the rotatable member, which are actively engaged in tissue morselization, differs from the pitch of the helical blades that are disposed within the hollow elongate body, which do not engage in tissue morselization, but are engaged in the transport of tissue, therapeutic agent, bulking agent etc. These and other embodiments (for instance, where a different type of morselizing tip besides an auger tip is desired) can be implemented by providing the rotatable member of the device with a detachable morselizing tip, thereby permitting a variety of morselizing tips to be used with a variety of shafts.

In some embodiments the shaft of the rotatable member is provided with a central lumen 120l allowing a solution 140, for example, an irrigation solution and/or a therapeutic agent solution to be introduced, even as the shaft is rotated in a direction that removes material away from the distal end of the device.

Figure 2:
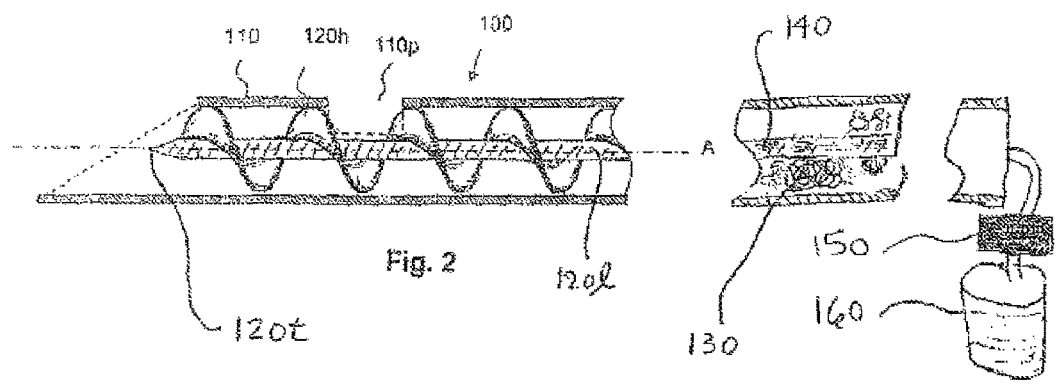
FIG. 2 is an schematic, partial cross-sectional illustration of the distal portion of a medical device, in accordance with another embodiment of the present invention.

FIG. 2 is similar to FIG. 1, except that the hollow elongate body 110 is provided with a side port 110p which can be used to facilitate tissue biopsy. As in FIG. 1, the hollow elongate body 110 is shown in cross section, while the rotatable member 120 is not. For example, a vacuum can be applied to the interior of the hollow elongate body 110 by placing a vacuum pump in communication with the distal end of hollow elongate body 110 (not shown), drawing tissue into the aperture where it is can be severed, for example, by the progressive movement of the helical blade 120h upon rotation of the same. For this purpose, the helical blade 120h may be provided with a sharp cutting edge, at least in the vicinity of the side port 110p where tissue is engaged.

Applying a vacuum to the interior of the hollow elongate body is also advantageous in various embodiments, as it can assist with both tissue morselization and the removal of morselized tissue. For example, a vacuum can assist the intake of tissue into the port at the end of the cylinder. The vacuum can also assist with movement of morselized tissue along the length the hollow elongate body where it is collected in a tissue recovery container positioned at the proximal end of the hollow elongate body. A vacuum pump can be connected to the tissue recovery container in this embodiment.

Analogously and conversely, placing the output of a fluid pump 150 in communication with the proximal end of the hollow elongate body is also advantageous in some embodiments as it can assist with the introduction of therapeutic agents and/or bulking agents into the patient. For example, the fluid pump 150 can pump therapeutic agent and/or bulking agent from a container 160 of the same (e.g., an ampoule) and can assist the rotating shaft in its movement of the therapeutic agent and/or bulking agent through the length of the hollow elongate body, whereupon it emerges from the distal end of the hollow elongate body and is introduced into the patient.

During treatment, the medical devices of the present invention are inserted into tissue of a patient, typically following either local or general anesthesia. In general, the distal end of the devices of the present invention are adapted to pierce tissue as discussed above. However, in some embodiments, the device is inserted into a previously established surgical incision to remove tissue, or deliver a desired therapeutic agent and/or an injectable material for bulking purposes.

Figure 3:
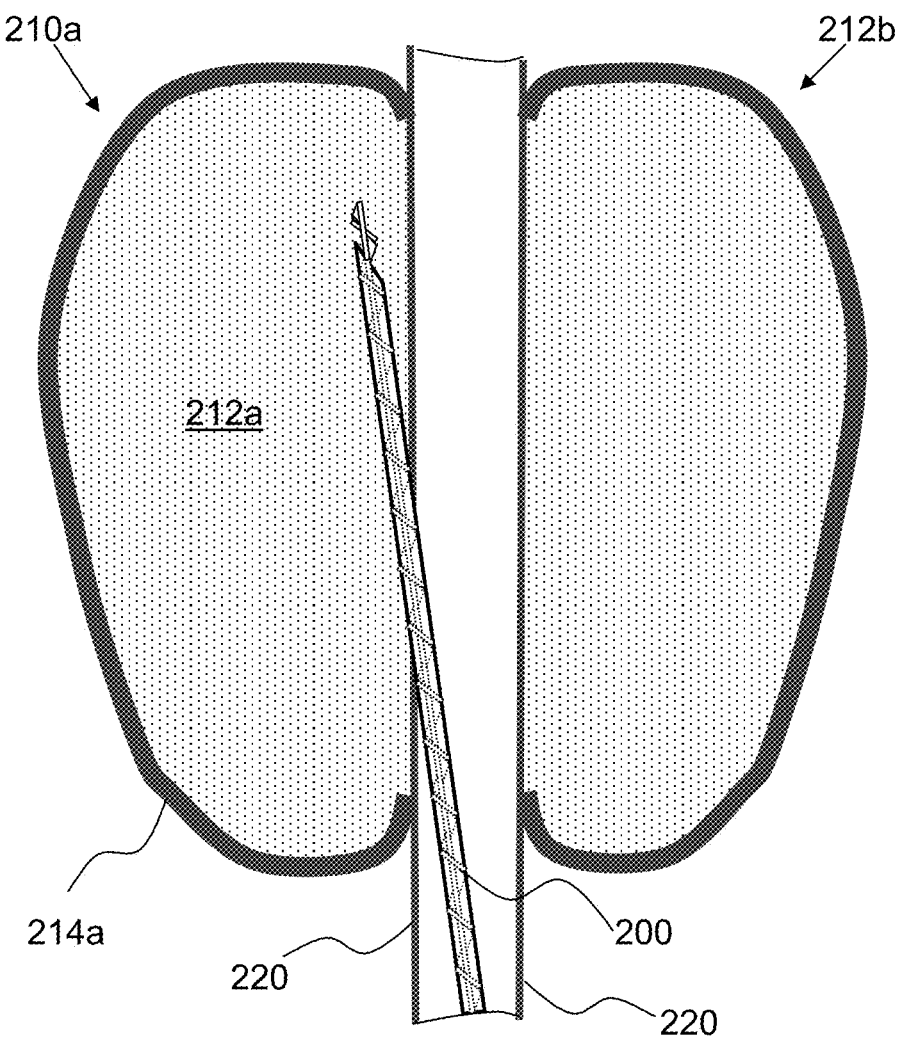
FIG. 3 is an schematic, partial cross-sectional illustration of the distal portion of a medical device inserted into one lobe of a prostate gland via the urethra, in accordance with an embodiment of the present invention.

In certain embodiments, the medical device is adapted to access tissue through a body lumen. As a specific example, FIG. 3 illustrates a medical device 200 which accesses prostatic tissue 212a within one lobe 210a of a prostate gland via the urethra 220 (the other lobe of the prostate is designated 212b in FIG. 3). As with various other bodily tissues, the prostatic tissue 212a is confined by a capsular membrane 214a.

Once positioned at the intended site, the shaft of the medical device is rotated in a first direction to morselize tissue and transport it down the length of the hollow elongate body of the medical device. In certain embodiments, the rotating member is axially extended beyond the distal end of the hollow elongate cylinder after insertion and prior to tissue morselization. After the operator determines that a sufficient amount of tissue has been extracted from the patient, the shaft of the medical device may be rotated in the opposite direction to direct therapeutic agent and/or bulking agent into the void created by the morselization process.

Therapeutic agents that can be introduced into the void include anticoagulants (e.g., to assist with tissue removal), hemostatic agents (e.g., to reduce bleeding), necrosis agents (e.g., to destroy further tissue), and antineoplastic agents (e.g., to combat cancer), among others, which are described below.

Subjects (also referred to as patients) for the various procedures of the present invention include vertebrate subjects, typically mammalian subjects, more typically human subjects.

A wide range of tissue can be extracted and treated using the devices of the present invention. Commonly, the tissue to be extracted and treated is, for example, prostatic tissue, kidney tissue, liver tissue, bladder tissue, brain tissue, among other soft tissues. The tissue may comprise benign tissue or malignant tissue. For example, in the case of the prostate, disease states for which the treatment may be useful include, BPH and prostate cancer.

The medical devices of the present invention can enter tissue by any of a wide variety of routes including transabdominal, transperineal, transcutaneous, transvascular, transurethral, transureteral, transoral, and transrectal routes of insertion. Other routes are suitable, depending on the location of the tissue. Where prostatic tissue is to be treated, transperineal, transurethral, and transrectal routes are typically used.

Due to the design and construction of the medical devices of the present invention, therapeutic agents and/or bulking agents can be introduced to the patient in a wide variety of dosage forms, including liquid, semi-liquid, semi-solid and solid dosage forms.

Liquid and semi-liquid dosage forms include solutions, solid-liquid suspensions, liquid-liquid emulsions and gels. In some embodiments, the liquid or semi-liquid dosage form consists essentially of the bulking agent or therapeutic agent (e.g., the use of ethanol as an ablation agent is one specific example). In other embodiments, the liquid and semi-liquid dosage forms contain additional components in addition to an effective amount of the therapeutic agent and bulking agent, such as optional solvents, optional diluents, optional carriers, optional surfactants, optional contrast agents, and so forth.

For example, where the dosage form is a solution, the therapeutic agent and/or bulking agent is dissolved in a solvent (e.g., an aqueous or organic solvent). Solid-liquid suspensions commonly comprise a solid suspension of particles containing the therapeutic agent and/or bulking agent within a liquid carrier. If desired, surface active agents (e.g., suspending agents) are utilized to stabilize the suspension. Liquid-liquid emulsions commonly comprise a disperse liquid phase (e.g., an organic phase comprising the therapeutic agent) within a continuous liquid phase (e.g., an aqueous phase comprising water). Analogous to solid dispersions, surface active agents (e.g., emulsifying agents) can be utilized to stabilize the emulsion, if desired. When forming a gel, a viscosity adjusting agent is typically included to adjust the viscosity. By providing highly viscous dosage forms, for example, dosage forms having a kinematic viscosity between about 5,000 and 200,000 cps, more typically between about 10,000 and 100,000 cps, the dosage forms are readily introduced to the tissue using the devices of the present invention, while at the same time having improved retention within the tissue due to the elevated viscosities. Further information regarding the viscosity adjusting agents and contrast agents can be found, for example, in U.S. Ser. No. 10/667,151, filed Sep. 18, 2003 and entitled "Injectable therapeutic formulations," the disclosure of which is hereby incorporated by reference.

Semi-solid and solid dosage forms for use in the methods and devices of the present invention may be in any form that can be transported via rotation of the rotating shaft, including powders, granules and small pellets, which may be, for example, rigid or deformable. In some embodiments, the solid dosage form consists essentially of the bulking agent and/or therapeutic agent (e.g., the use of particles as a bulking agent and salt as an ablation agent is one specific example). In other embodiments, other supplemental components are provided in addition to an effective amount of the therapeutic agent and/or bulking agent, such as optional diluents, optional binders (e.g., a biodisintegrable polymer or organic compound), optional contrast agents, and so forth. For further information regarding binders and contrast agents, see, e.g., U.S. Ser. No. 10/664,601, filed Sep. 18, 2003 and entitled "Solid or semi-solid therapeutic formulations," the disclosure of which is hereby incorporated by reference.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature.

Exemplary non-genetic therapeutic agents for use in connection with the present invention include: (a) anti-thrombotic agents such as heparin, heparin derivatives, urokinase, and Ppack (dextrophenylalanine praline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, Epo D, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, cilostazole, thienopyridine (ticlopidine, clopidogrel), GP IIb/IIIa inhibitors such as abciximab, epitifibatide and tirofiban, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins;

(l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin; (t) matrix deposition/organization pathway inhibitors such as halofuginone or other quinazolinone derivatives and tranilast; (u) analgesics including opioid analgesics, such as codeine, fentanyl, meperidine, methadone, morphine, pentazocine, and tramadol, and non-opioid analgesics, such as etodolac, fenoprofen, ketoprofen, ketorolac, mefenamic acid, paracetamol, and piroxicam, as well as non-steroidal anti-inflammatory drugs, such as aspirin, diclofenac, ibuprofen, indomethacin, and naproxen; (w) antispasmodic/anitcholinergic agents including oxybutynin (e.g., oxybutynin chloride), hyoscyamine (e.g., hyoscyamine sulfate) and flavoxate (e.g., flavoxate HCl); (v) local anesthetic agents including amino amides such as lidocaine, mepivacaine, prilocaine, bupivacaine, etidocaine, and dibucaine, and amino esters such as tetracaine, procaine, chloroprocaine, cocaine, and benzocaine; and (w) additional salts of the foregoing as well as combinations of the forgoing.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

As noted above, in certain embodiments of the invention, the therapeutic agent is selected from anticoagulants, antispasmodic/anitcholinergic agents, local anesthetic agents, hemostatic agents, necrosis agents, and antineoplastic agents. Some examples of anticoagulants, antispasmodic/anitcholinergic agents and local anesthetic agents are set forth above. Several examples of the other agents, not necessarily exclusive of those listed above, follow.

Examples of known hemostatic agents, include adrenalone, adrenochrome, aminochrome, batroxobin, carbazochrome salicylate, carbazochrome sodium sulfonate, cephalins, cotarnine, ethamsylate, factors VIII, IX and XIII, fibrinogen, 1,2-naphthoquinone, 1-naphthylamine-4-sulfonic acid, oxamarin, oxidized cellulose styptic collodion, sulmarin, thrombin, thromboplastin, tolonium chloride, tranexamic acid, vasopressin, and vitamins K2, K5 and K-S(II).

Ablation/necrosis agents are materials whose introduction to the tissue will result in necrosis (death) of tissue. Examples of ablation/necrosis agents include the following: (a) osmotic-stress-generating agents, for example, a salt, such as sodium chloride or potassium chloride; (b) organic compounds that are toxic in high concentrations, while being non-toxic at lower concentrations, for example, an alcohol such as ethanol (note that alcohols, like salt, can also dehydrate cells and tissues causing them to shrink and die); (c) free-radical generating agents, for example, hydrogen peroxide, potassium peroxide or other agents that can form free radicals in tissue, for example, by decomposition of the free-radical generating agent upon exposure to water, exposure to heat, exposure to light and/or exposure to exposure to other agents; (d) basic agents such as sodium hydroxide; (e) acidic agents such as acetic acid and formic acid; (f) enzymes such as collagenase, hyaluronidase, pronase, and papain; and (g) oxidizing agents such as sodium hypochlorite, hydrogen peroxide or potassium peroxide; (h) tissue fixing agents such as formaldehyde, acetaldehyde or glutaraldehyde, and (i) naturally occurring coagulants such as gengpin.

Examples of known antineoplastic agents include: (a) alkaloids such as docetaxel, etoposide, irinotecan, paclitaxel, teniposide, topotecan, vinblastine, vincristine and vindesine; (b) alkylating agents, including (i) alkyl sulfonates such as busulfan, improsulfan and piposulfan, (ii) aziriaines such as benzodepa, carboquone, meturedepa and uredepa, (iii) ethyleneimines and methylmelamines such as altretamine, triethylenemelamine, triethylenephosphoramide, triethylenethiophosphoramide and trimethylolmelamine, (iv) nitrogen mustards such as chlorambucil, chlornaphazine, cyclophosphamide, estramustine, ifosfamide, mechlorethamine, mechlorethamine oxide hydrochloride, melphalan, novembichin, perphosfamide, phenesterine, prednimustine, trofosfamide, and uracil mustard, (v) nitrosoureas such as carmustine, chlorozotocin, fotemustine, lomustine, nimustine and ranimustine, and (vi) other alkylating agents such as dacarbazine, mannomustine, mitobronitol, mitolactol, pipobroman and temozolomide; (c) antibiotics and their analogs, including aclacinomycins, actinomycin $F_1$, anthramycin, azaserine, bleomycins, cactinomycin, carubicin, carzinophilin, chromomycins, dactinomycin, daunorubicin, 6-diazo-5-oxo-leucine, doxorubicin, epirubicin, idarubicin, menogaril, mitomycins, mycophenolic acid, nogalamycin, olivomycins, peplomycin, pirarubicin, plicarmycin, porfiromycin, puromycin, streptonigrin, streptozocin, tubercidin, zinostatin and zorubicin; (d) antimetabolites, including (i) folic acid analogs such as denopterin, edatrexate, methotrexate, piritrexin, pteropterin, Tomudex®, and trimetrexate, (ii) purine analogs such as cladribine, fludarabine, 6-mercaptopurine, thiamiprine, thioguanine, and (iii) pyrimidine analogs such as ancitabine, azacitidine, 6-azauridine, carmofur, cytarabine, doxifluridine, emitefur, enocitabine, floxuridine, fluorouracil, gemcitabine and tegafur; (e) enzymes such as 1-asparaginase; (f) immunomodulators such as interferon-α, interferon-β, interferon-γ, interleukin-2, lentinan, propagermanium, PSK, roquinimex, sizofiran, ubenimex; (g) platinum complexes such as carboplatin, cisplatin, miboplatin, oxaliplatin, (h) other antineoplastics such as aceglatone, amsacrine, bestrabucil, bisantrene, defosfamide, demecolcine, diaziquone, eflorithine, elliptinium acetate, etoglucid, fenretinide, gallium nitrate, hydroxyurea, lonidamine, miltefosine, mitoguazone, mitoxantrone, mopidamol, nitracrine, pentostatin, phenamet, podophyllinic acid 2-ethylhydrazide, procarbazine, razoxane, sobuzoxane, spirogermanium, tenuazonic acid, triaziquone, 2,2',2''-trichlorotriethylamine and urethan; (i) androgens such as calusterone, dromostanolone, epitiostanol, mepitiostane, testolactone; (j) antiadrenals such as aminoglutethimide, mitotane, trilostane; (k) antiandrogens such as bicalutamide, flutamide and nilutamide; (l) antiestrogens such as droloxifene, tamoxifen, toremifene; (m) aromatase inhibitors such as aminoglutethimide, anastrozole, fadruzole, formestane, and letrozole; (n) estrogens such as fosfestrol, hexestrol and polyestradiol phosphate; (o) LHRH analogs such as buserelin, goserelin, leuprolide and triptorelin; and (p) antineoplastic radiation sources such as americium, cobalt, $^{131}$I-ethiodized oil, gold (radioactive and colloidal), radium, radon, sodium iodide (radioactive) and sodium phosphate (radioactive).

A wide range of therapeutic agent loadings can be used in conjunction with the above dosage forms, with the effective amount of loading being readily determined by those of ordinary skill in the art and ultimately depending, for example, upon the nature of the therapeutic agent, the tissue into which the dosage forms are introduced, the disease or condition to be treated, the presence of other components in the dosage form, and so forth.

Also useful in conjunction with the dosage forms of the present invention are bulking agents, which increase tissue bulk (e.g., in the treatment of stress incontinence). Suitable bulking agents include, for example, effective amounts of the following: (a) inorganic bulking agents, for instance, ceramics and glass ceramics (e.g., biogas), as well as carbon coated beads (e.g., carbon-coated zirconium oxide beads available as Dresher™); (b) synthetic polymers such as silicones (e.g. silicone micro-implants), polyvinyl alcohol (e.g., polyvinyl alcohol foam), polyvinyl acetate, dextranomer (e.g., dextranomer particles in hyaluronan solution, available as Deflux®); (c) biopolymers including proteins (e.g., crosslinked collagen available as Contigen™); (d) autologous materials such as the patient's own fat, collagen, bladder cells, smooth muscle cells, chondrocytes, stem cells, and myoblasts; and (e) agents that promote a foreign response (e.g., sclerosing agents such as paraffin or Dondren).

Non-invasive imaging is a valuable tool for use in conjunction with the present invention. For example, imaging guidance, either internal or external, can be used to determine the location of the medical device (or a component thereof, e.g., the hollow elongate body, the rotatable member, etc.), the location of the tissue to be removed, and/or the location of any therapeutic agent or bulking agent that is introduced. Consequently, the dosage forms and medical devices for use in connection with the present invention also optionally include an effective amount of one or more imaging contrast agents (i.e., substances that enhance the image produced by medical diagnostic equipment). Among currently available contrast agents are magnetic resonance imaging (MRI) contrast agents, ultrasonic imaging contrast agents, x-ray fluoroscopy contrast agents, nuclear medicine contrast agents, and others.

For example, x-ray based fluoroscopy is a diagnostic imaging technique that allows real-time patient monitoring of motion within a patient. To be fluoroscopically visible, devices and/or formulations are typically rendered more absorptive of x-rays than the surrounding tissue (e.g., radiopaque materials). In various embodiments of the invention, this is accomplished by the use of contrast agents. Examples of contrast agents for use in connection with x-ray fluoroscopy include metals, metal salts and oxides (particularly bismuth salts and oxides), and iodinated compounds. More specific examples of such contrast agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine.

Ultrasound and magnetic resonance imaging can provide two-and/or three-dimensional images of a portion of the body. Ultrasound and MRI are advantageous, inter alia, because they do not expose the patient or medical practitioner to harmful radiation and can provide detailed images of the observed area.

Ultrasound uses high frequency sound waves to create an image of living tissue. A sound signal is sent out, and the reflected ultrasonic energy, or "echoes," used to create the image. Ultrasound imaging contrast agents are materials that enhance the image produced by ultrasound equipment. Ultrasonic imaging contrast agents introduced into the formulations and medical devices of the present invention can be, for example, echogenic (i.e., materials that result in an increase in the reflected ultrasonic energy) or echolucent (i.e., materials that result in a decrease in the reflected ultrasonic energy).

Suitable ultrasonic imaging contrast agents for use in connection with the present invention include solid particles ranging from about 0.01 to 50 microns in largest dimension (e.g., the diameter, where spherical particles are utilized), more typically about 0.5 to 20 microns. Both inorganic and organic particles can be used. Examples include microparticles/microspheres of calcium carbonate, hydroxyapatite, silica, poly(lactic acid), and poly(glycolic acid). Microbubbles can also be used as ultrasonic imaging contrast agents, as is known in the imaging art.

Magnetic resonance imaging (MRI) produces images by differentiating detectable magnetic species in the portion of the body being imaged. In the case of $^1$H MRI, the detectable species are protons (hydrogen nuclei). In order to enhance the differentiation of detectable species in the area of interest from those in the surrounding environment, imaging contrast agents are often employed. These agents alter the magnetic environment of the detectable protons in the area of interest relative to that of protons in the surrounding environment and, thereby, allow for enhanced contrast and better images of the area of interest. For contrast-enhanced MRI, it is desirable that the contrast agent have a large magnetic moment, with a relatively long electronic relaxation time. Based upon these criteria, contrast agents such as Gd(III), Mn(II) and Fe(III) have been employed. Gadolinium(III) has the largest magnetic moment among these three and is, therefore, a widely-used paramagnetic species to enhance contrast in MRI. Chelates of paramagnetic ions such as Gd-DTPA (gadolinium ion chelated with the ligand diethylenetriaminepentaacetic acid) have been employed as MRI contrast agents. Chelation of the gadolinium or other paramagnetic ion is believed to reduce the toxicity of the paramagnetic metal by rendering it more biocompatible, and can assist in localizing the distribution of the contrast agent to the area of interest. Further information can be found, for example, in U.S. Patent Application No. 20030100830 entitled "Implantable or insertable medical devices visible under magnetic resonance imaging," the disclosure of which is incorporated herein by reference.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising: (a) a hollow body having an open distal end and a proximal end; and (b) a rotatable shaft comprising a tissue morselizer portion and a raised helical blade extending along at least a portion of the rotatable shaft, said rotatable shaft disposed within said hollow body and cooperating with said hollow body to (i) advance at least a first material toward the proximal end of said hollow body when said rotatable shaft is rotated in a first direction, and (ii) advance at least a second material toward the distal end from the proximal end of said hollow body when said rotatable shaft is rotated in a second direction that is opposite said first direction.

2. The medical device of claim 1, wherein said distal end of said hollow body is adapted for penetration of tissue.

3. The medical device of claim 1, wherein said hollow body comprises a hollow needle.

4. The medical device of claim 3, wherein said hollow needle further comprises a side port.

5. The medical device of claim 1, wherein said rotatable shaft comprises two or more raised helical portions.

6. The medical device of claim 1, wherein said tissue morselizer portion comprises a tissue-morselizing auger bit forming a distal end of the rotatable shaft.

7. The medical device of claim 1, wherein said rotatable shaft is axially moveable with respect to said hollow body.

8. The medical device of claim 1, wherein said rotatable shaft is hollow.

9. The medical device of claim 1, wherein said tissue morselizer portion is adapted to morselize tissue at the distal end of said hollow body.

10. The medical device of claim 1, wherein said medical device is adapted for insertion into a body lumen and wherein said distal end of said hollow member is adapted to pierce the wall of said body lumen and access a tissue region proximate said body lumen.

11. The medical device of claim 1, further comprising a tissue collection container in communication with the proximal end of said hollow body.

12. A system for tissue removal comprising: (a) the medical device of claim 1 and (b) a reservoir source of at least one of a therapeutic agent and a bulking agent.

13. The system of claim 12, wherein the reservoir source includes the therapeutic agent, and wherein said therapeutic agent is selected from anticoagulants, analgesics, antispasmodic agents, hemostatic agents, necrosis agents and antineoplastic agents.

14. The system of claim 12, wherein at least one of said therapeutic agent and said bulking agent is in particulate, granulated or pelletized dosage form.

15. A method of treatment comprising:
inserting a medical device into tissue of a patient, wherein the medical device includes a hollow body having an open distal end and a proximal end, and a shaft located within the hollow body, the shaft having a morselizing portion and a raised helical blade;
morselizing and removing tissue proximally through the hollow body from within said patient while rotating said shaft in a first direction, thereby creating a void within said patient; and
introducing through the medical device at least one of a therapeutic agent or a bulking agent into said void by rotating said shaft in a second direction.

16. The method of claim 15, wherein said tissue removal further includes applying a vacuum.

17. The method of claim 15, wherein said tissue is selected from prostate, brain, or soft cancer tissue.

18. The method of claim 15, wherein said therapeutic agent is selected from anticoagulants, analgesics, antispasmodic agents, hemostatic agents, necrosis agents, or antineoplastic agents.

* * * * *